(12) United States Patent
Biedermann et al.

(10) Patent No.: US 6,736,820 B2
(45) Date of Patent: May 18, 2004

(54) BONE SCREW

(75) Inventors: Lutz Biedermann, VS-Villingen (DE); Jürgen Harms, Karlsruhe (DE)

(73) Assignee: Biedermann Motech GmbH, Schwenningen (DE)

(*) Notice: Subject to any disclaimer, the term of this patent is extended or adjusted under 35 U.S.C. 154(b) by 0 days.

(21) Appl. No.: 10/037,698

(22) Filed: Nov. 9, 2001

(65) Prior Publication Data

US 2002/0058942 A1 May 16, 2002

(30) Foreign Application Priority Data

Nov. 10, 2000 (DE) .......................... 100 55 888
Dec. 27, 2000 (DE) .......................... 100 65 397

(51) Int. Cl.[7] .............................................. A61B 17/56
(52) U.S. Cl. ............................ 606/73; 606/72; 606/69
(58) Field of Search ............................ 606/73, 69, 70, 606/71, 72, 61

(56) References Cited

U.S. PATENT DOCUMENTS

| 5,057,111 A | 10/1991 | Park ........................ 606/69 |
| 5,672,176 A | 9/1997 | Biedermann et al. ......... 606/61 |
| 5,891,145 A | 4/1999 | Morrison et al. ............. 606/61 |
| 5,954,725 A | 9/1999 | Sherman et al. ............. 606/78 |
| 6,139,550 A | 10/2000 | Michelson ................... 606/69 |
| 2003/0055426 A1 | 3/2003 | Carbone et al. |

FOREIGN PATENT DOCUMENTS

WO    WO 98/34554    8/1998

*Primary Examiner*—Cary E. O'Connor
*Assistant Examiner*—Candice C. Melson
(74) *Attorney, Agent, or Firm*—George W. Neuner; Edwards & Angell LLP

(57) ABSTRACT

A bone screw having a screw member (1) possessing a threaded section (2) and a head (3) and a receiving part (5) at the head end for receiving a rod to be connected to the bone screw is provided. The receiving part (5) has on open first bore (6) and a substantially U-shaped cross-section having two free legs provided with a thread. Furthermore, the receiving part has a second bore (7) on the end opposite to the first bore (6) whose diameter is greater than that of the threaded section (2) and smaller than that of the head (3). On the bottom of the first bore a seat for the head (3) is provided. In order that the screw member can be pivoted to at least one side by an enlarged angle, the edge bounding the free end of the second bore (7) viewed relative to the axis of the first bore (6) is of asymmetric construction.

8 Claims, 1 Drawing Sheet

BONE SCREW

BACKGROUND OF THE INVENTION

The invention relates to a bone screw having a threaded section and a head and a receiving part at the head end for receiving a rod to be connected to the bone screw, the receiving part possessing an open first bore and a substantially U-shaped cross-section having two free legs provided with a thread and a second bore at the end opposite to the first bore, whose diameter is greater than that of the threaded section and smaller than that of the head and which forms the seat for the head, and a nut or screw working together with the thread.

Such a bone screw is disclosed, for example, in U.S. Pat. No. 5,672,176. In the known bone screw the head is of spherical segment-shaped construction. The bottom of the first bore adjacent to the second bore is likewise of spherical segment-shaped construction so that the spherical head lies on this spherical section. The plane going through the bounding edge is oriented at right angles to the axis of the first bore and the mid-point of the second bore coincides with the axis of the first bore. By this means it is achieved that the threaded section possessing the head is pivotable in a predetermined angle of generally up to 25° about the axis of the first bore so that even after screwing the threaded section into a vertebral segment orientation of the receiving part receiving a rod is possible. At the same time the size of the pivot angle is limited to the extent that the second bore as a function of the diameter of the head must not exceed a certain size so that the head still has an adequate hold in the receiving part.

The use of such bone screws is something of a problem in the region of cervical vertebrae. In this case, due to the small dimensions of the cervical vertebrae, it is necessary that the screws must always be pivoted to one side and upwards, a greater degree of pivoting being necessary than is the case in the larger thoracic vertebrae and lumbar vertebrae.

SUMMARY OF THE INVENTION

The aim of the invention is to provide a bone screw which permits a larger pivot angle. This task is solved by a bone screw having a screw member 1 possessing a threaded section 2 and a head 3, a receiving part 5 at the head end for receiving a rod to be connected to the bone screw, wherein the receiving part 5 has an open first bore 6 and a substantially U-shaped cross-section having two free legs provided with a thread, and a second bore 7 at the end opposite to the first bore 6 whose diameter is greater than that of the threaded section 2 and smaller than that of the head 3, and a seat for the head 3 and a nut or screw acting together with the thread, characterised in that viewed relative to the axis of the first bore 6 the edge bounding the free end of the second bore 7 is of asymmetric construction.

Refinements of the invention are characterised in that (i) the bounding edge has a countersink 10 in an angular region, (ii) the normal to the plane going through the bounding edge is inclined to the axis of the first bore 6, and (iii) the mid-point of the plane enclosed by the bounding edge is offset relative to the axis of the first bore 6.

In a preferred embodiment of the invention, a bone screw has a screw member 1 possessing a threaded section 2 and a head 3, a receiving part 5 at the head end for receiving a rod to be connected to the bone screw, wherein the receiving part 5 has an open first bore 6 and a substantially U-shaped cross-section having two free legs provided with a thread, and a second bore 7 at the end opposite to the first bore 6 whose diameter is greater than that of the threaded section 2 and smaller than that of the head 3, and a seat for the head 3 and a nut or screw acting together with the thread, characterised in that on its neck adjoining the spherical segment the screw member 1 has a recess or sink 16.

Further features and practical advantages of the invention emerge from the description of exemplified embodiments with reference to the figures.

DETAILED DESCRIPTION OF THE INVENTION INCLUDING PREFERRED EMBODIMENTS

Figure 1:
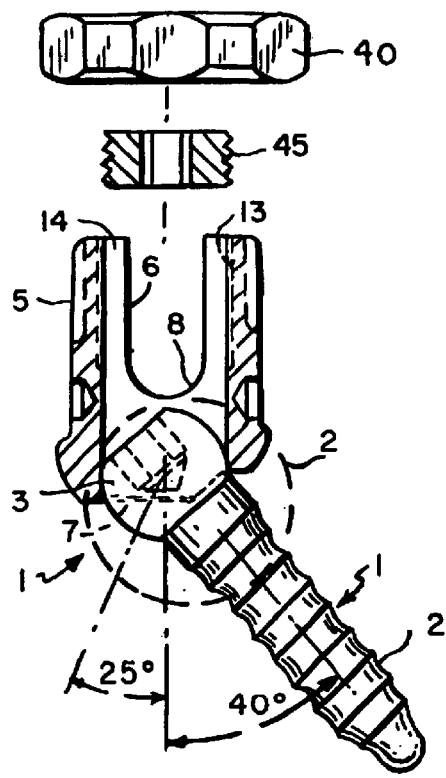
FIG. 1 a side elevation of a first embodiment, partly in sectional representation.

The bone screw further comprises a cylindrically constructed receiving part 5. At one end this has a first bore 6 of axially symmetrical construction. On the opposite end a second bore 7 is provided whose diameter is greater than that of the threaded section 2 and smaller than that of the head 3. On the end opposite to the second bore the first bore is open and its diameter is of such a size that the screw member 1 can be guided through the open end by its threaded section 2 going through this bore and by the head going as far as the bottom of the first bore. The bottom of the first bore is constructed as a spherically shaped region towards the open end, the radius being substantially equal to the radius of the spherical segment-shaped section of the head 3. Furthermore, the receiving part 5 has a U-shaped recess 8 arranged symmetrically relative to the centre of the part whose bottom is directed towards the second bore 7 and whose two side legs 13, 14 extend to the open end directed towards the first bore 6. At the free end of the legs 13, 14 a thread for engagement with a screw member constructed as a nut 40 or screw 45 is provided. The nut or screw serves to fix a rod to be inserted into the U-shaped recess 8, it being possible for the nut or screw to act on the rod directly or via a pressure member.

Figure 2:
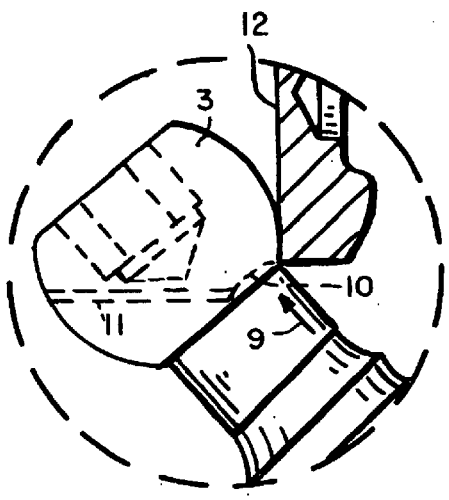
FIG. 2 an enlarged detail of FIG. 1.

In the embodiment shown in FIGS. 1 and 2, in the direction of the arrow 9, whose direction lies in a plane going through the axis of symmetry of the first bore and which is inclined to the axis of symmetry by a predetermined angle, a circular countersink 10 is made in the edge between the opening plane 11 of the second bore and the edge 12 of the first bore.

In this manner, as can be seen in the figures, it is achieved that the angle between the axis of the screw member 1 and the axis of symmetry of the first bore is substantially enlarged by comparison with the angle otherwise attainable. At the same time the seat of the screw member 1 in the receiving part is retained.

Figure 3:
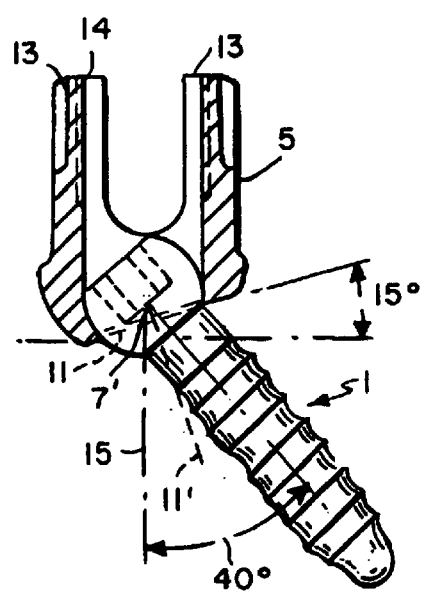
FIG. 3 a side elevation, partly in sectional representation, of a second embodiment.

In the second embodiment shown in FIG. 3 the interior of the receiving part 5 is constructed as in the first embodiment. The opening plane 11, which bounds the second bore 7, in this embodiment is inclined at a predetermined angle α to the plane bounded by the second bore 7 so that the normal 11' to this plane 11 and the axis of symmetry of the first bore 15 enclose the angle of inclination. In the case shown this angle α is 15° as an exemplified embodiment. In this version it is also achieved that the screw member 1 is pivotable in the direction shown by an angle to the axis of symmetry of the first bore which is substantially greater than the angle which is achievable in the usual mode of construction.

Both in the embodiment shown in FIG. 1 and the embodiment shown in FIG. 3 the countersink or chamfer is selected in such a way that in each case a small peripheral section still remains which still belongs to the spherical seat.

In a fourth embodiment which is not shown the mid-point 7' of the second bore is constructed offset to the side to a small extent, for example by 0.5 mm, relative to the axis of symmetry of the first bore. This lateral offsetting in turn produces the result that the head is held in the mounting formed by the spherically constructed bottom but a greater pivot width is achieved in a side direction.

In the exemplified embodiments described above four different approaches to a solution are presented. It is also possible to combine the individual approaches with one another, that is, for example, to combine the solution according to the first and second exemplified embodiments or one of the two with the third and/or fourth exemplified embodiment, or even all four exemplified embodiments in order to achieve, in this way, a still greater possibility for pivoting in at least one direction.

In the exemplified embodiments described above the spherical bottom of the first bore 6 is constructed in each case as an integral component of the receiving part 5. In a modified embodiment, however, the spherical bottom can also be provided either in a mounting part introduced through the first bore 6 or in a mounting part introduced through the second bore 7. The invention is then used in a corresponding manner to the end that the receiving part together with the insert piece is regarded as one member and the measures described above are taken on this piece assembled in this way.

The members forming the bone screw are preferably made of titanium.

Figure 4:
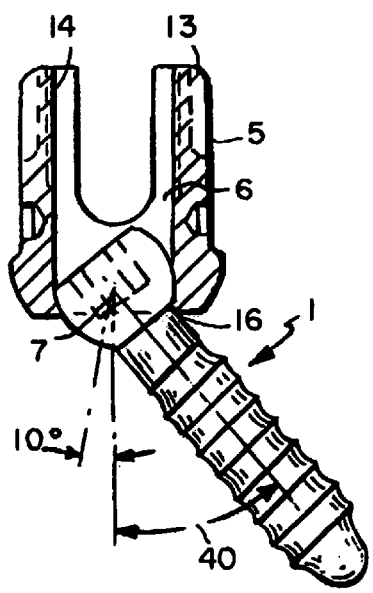
FIG. 4 a corresponding representation of a further embodiment.

In the embodiment shown in FIG. 4 the edge bounding the free end of the second bore viewed relative to the axis of the first bore is of symmetrical construction. The asymmetry is achieved in that the screw 1 has a recess or countersink 16 on its neck engaging on the sphere or the spherical segment so that in the manner shown in FIG. 4 as in the exemplified embodiments previously described the enlarged pivot angle can be achieved.

What is claimed is:

1. A bone screw apparatus comprising:
   a bone screw having a screw member a threaded section, a head end and a head at the head end;
   a receiving part at the head end for receiving a rod to be connected to the bone screw, wherein the receiving part has an open first bore with an axis and a substantially U-shaped cross-section having two free legs provided with a thread, and a second bore at an end opposite to the first bore, the second bore having a free end with an edge and a diameter is greater than that of the threaded section and smaller than that of the head, and a seat for the head; and
   a nut or screw acting together with the thread,
   wherein, when viewed relative to the axis of the first bore, the edge bounding the free end of the second bore is asymmetric.

2. A bone screw apparatus according to claim 1, wherein the edge has a countersink in an angular region.

3. A bone screw apparatus according to claim 1, wherein a normal to a plane going through the edge is inclined to the axis of the first bore.

4. A bone screw apparatus according to claim 1, wherein a mid-point of a plane enclosed by the edge is offset relative to the axis of the first bore.

5. A bone screw apparatus comprising:
   a bone screw having a screw member, a threaded section, a head end and a head being formed in the shape of a spherical segment in the region adjoining the threaded section at the head end;
   receiving part at the head end for receiving a rod to be connected to the bone screw, wherein the receiving part has an open first bore with an axis and a substantially U-shaped cross-section having two free legs provided with a thread, and a second bore at an end opposite to the first bore, the second bore having a free end with an edge and a diameter that is greater than that of the threaded section and smaller than that of the head, and a seat for the head; and
   a nut or screw acting together with the thread,
   wherein a recess or countersink is formed in the receiving part adjacent the spherical segment,
   wherein a normal to a plane going through the edge is inclined to the axis of the first bore.

6. A bone screw apparatus according to claim 5, wherein a mid-point of a plane enclosed by the edge is offset relative to the axis of the first bore.

7. A bone screw apparatus according to claim 5, wherein a mid-point of a plane enclosed by the edge is offset relative to the axis of the first bore.

8. A bone screw apparatus comprising:
   a bone screw having a screw member with a symmetry axis, a threaded section, a head end, a head being formed in the shape of a spherical segment in the region adjoining the threaded section at the head end and a neck adjoining the sperical segment;
   a receiving part at the head end for receiving a rod to be connected to the bone screw, wherein the receiving part has an open first bore with an axis and a substantially U-shaped cross-section having two free legs provided with a thread, and a second bore at an end opposite to the first bore, the second bore having a free end with an edge and a diameter that is greater than that of the threaded section and smaller than that of the head, and a seat for the head; and
   a nut or screw acting together with the thread,
   wherein the neck has a recess or countersink and is asymmetric with respect to the symmetry axis.

* * * * *

UNITED STATES PATENT AND TRADEMARK OFFICE
CERTIFICATE OF CORRECTION

| | |
|---|---|
| PATENT NO. | : 6,736,820 B2 |
| APPLICATION NO. | : 10/037698 |
| DATED | : May 18, 2004 |
| INVENTOR(S) | : Lutz Biedermann et al. |

It is certified that error appears in the above-identified patent and that said Letters Patent is hereby corrected as shown below:

On the Title Page

Item (73) Assignee    Delete "Schwenningen (DE)
                      Insert -- "VS-Schwenningen (DE) --

In the Specification

Column 2, line 25    After the heading

DETAILED DESCRIPTION OF THE INVENTION INCLUDING PREFERRED EMBODIMENTS

Insert -- The bone screw possesses the proper screw member 1 having a threaded section 2 and a head 3. The head is formed in the shape of a segment of a sphere in the region adjoining the threaded section. Coaxial with the thread axis and on the end opposite to the threaded section 2 the head possesses a recess 4 for engagement with a socket screw key. --

Signed and Sealed this
Thirteenth Day of May, 2014

Michelle K. Lee
*Deputy Director of the United States Patent and Trademark Office*